United States Patent [19]
Chu et al.

[11] Patent Number: 5,854,083
[45] Date of Patent: *Dec. 29, 1998

[54] POST SYNTHESIS CHEMICAL MODIFICATION OF PARTICLE REAGENTS

[75] Inventors: Victor Pichai Chu, Hockessin; Alan Robert Craig, Wilmington, both of Del.

[73] Assignee: Dade Behring Inc., Deerfield, Ill.

[ * ] Notice: This patent issued on a continued prosecution application filed under 37 CFR 1.53(d), and is subject to the twenty year patent term provisions of 35 U.S.C. 154(a)(2).

[21] Appl. No.: 510,687

[22] Filed: Aug. 3, 1995

[51] Int. Cl.$^6$ .................................................. G01N 33/546
[52] U.S. Cl. .......................... 436/523; 427/337; 427/338; 428/403; 435/7.1; 435/962; 436/518; 436/531; 436/532; 436/533; 436/815
[58] Field of Search ..................................... 427/337, 338; 428/403; 435/7.1, 962; 436/518, 523, 531, 532, 533, 815

[56] References Cited

U.S. PATENT DOCUMENTS

| | | | |
|---|---|---|---|
| 4,415,700 | 11/1983 | Batz et al. | 524/548 |
| 4,480,042 | 10/1984 | Craig et al. | 436/533 |

FOREIGN PATENT DOCUMENTS

| | | |
|---|---|---|
| 0 073 611 A1 | 3/1983 | European Pat. Off. . |
| 0 406 473 A1 | 1/1991 | European Pat. Off. . |

*Primary Examiner*—Christopher L. Chin
*Attorney, Agent, or Firm*—Lois K Ruszala

[57] ABSTRACT

A method is provided for enhancing the stability and increasing the activity of polymer particle reagents by incubating a polymer particle which has been covalently bound to a compound of biological interest, such as a drug, with a modifying agent that will place a negative charge on the surface of the polymer particle and reduce residual functional groups. The modifying agent is preferably an anionic nucleophile selected from the group consisting of β-mercaptoacetic acid and the thiosulfates.

16 Claims, 2 Drawing Sheets

FIG. 1A  COMPARATIVE STABILITY DURING STORAGE AT 35°
VANCOMYCIN REAGENT EXAMPLE 2B

FIG. 1B  COMPARATIVE STABILITY DURING STORAGE AT 35°
VANCOMYCIN REAGENT EXAMPLE 1A

FIG. 1C  COMPARATIVE STABILITY DURING STORAGE AT 35°
VANCOMYCIN REAGENT EXAMPLE 2A

FIG. 2

POST SYNTHESIS CHEMICAL MODIFICATION OF PARTICLE REAGENTS

BACKGROUND OF THE INVENTION

1. Field of the Invention

The invention relates to polymer particle reagents which possess high sensitivity for use in light-scattering agglutination assays, and more particularly, to particle reagents covalently bound via a functional group of compounds of biological interest, which particle reagents have been treated with a modifier to enhance reactivity and stability.

2. Description of the Invention Background

Particle reagents have been used as carriers for haptens, proteins or other compounds of biological interest in assays for the quantitative detection of bacteria, cell surface antigens, serum proteins or other analytes to provide increased sensitivity to visual or instrumental detection of agglutination reactions or the inhibition of agglutination. Various methods for the preparation of particle reagents are known.

Particle reagents having a polymer inner core with a high refractive index and a polymer outer shell with functional groups bound directly or indirectly to compounds of biological interest for use in sensitive light scattering immunoassays utilizing agglutination reactions or the inhibition of agglutination are described in U.S. Pats. Nos. 4,401,765 and 4,480,042.

Assays which employ polymer particle reagents for detecting the presence and quantifying the levels of various drugs in serum or other fluids by light scattering techniques are commercially available. It has been found that these polymer particle reagents, particularly those having epoxy functional groups on the outer shell of the polymer particle, lose activity when heated under alkaline conditions. This instability is seen even with storage at low temperatures and moderate pH, and is associated with loss of immunoreactivity. There is a need for a method of enhancing the stability of the polymer particle reagents without loss of activity. It is an object of the present invention to provide a particle reagent for use in light scattering immunoassays which has increased stability and immunoreactivity. It is a further object of the invention to provide a process for the production of such a particle reagent.

SUMMARY OF THE INVENTION

The objects of the present invention are provided by a process for improving the stability and increasing the immunoreactivity of a particle reagent which comprises a polymer particle covalently bound to a compound of biological interest. The method includes the steps of synthesizing the polymer particle reagent by covalently binding reactive functional groups of the polymer particles to complementary functional groups of compounds of biological interest, then incubating the polymer particle reagent under predetermined pH and temperature conditions with a modifying agent that places a negative charge on the particle surface. Preferred modifiers are anionic nucleophiles selected from the group consisting of β-mercaptoacetic acid and thiosulfate. Non-limiting examples of functional groups on the particle include those containing epoxy, carboxyl, hydroxyl, amino and aldehyde groups. The compounds of biological interest include serum, plasma, salivary, urinary or milk proteins; drugs, vitamins, hormones, enzymes, antibodies, polysaccharides, bacteria, protozoa, fungi, viruses, cell and tissue antigens and other blood cell or blood fluid substances. The compound may be linked to the polymer shell directly, through a synthetic spacer arm, or through a proteinaceous material. Where the compound is a drug it may be selected from the group consisting of quinidine, phenobarbital and the amino glycoside antibiotics, such as vancomycin, tobramycin and gentamycin. The compound of biological interest preferably has a molecular weight of less than 2000.

The polymer particle reagent may be any suitable known particle reagent. A preferred reagent is comprised of (A) a polymer particle having an inner core and an outer shell wherein the inner core is a polymer having a refractive index of not less than 1.54 as measured at the wavelength of the sodium D line and the outer shell is a polymer of an ethylenically unsaturated monomer having the residue of a nucleophilic functional group capable of reacting with a complementary functional group of a compound of biological interest, and which is covalently bound to (B) a compound of biological interest.

The polymer particle reagent produced by the process of the present invention may be used in light scattering immunoassays for measuring compounds of biological interest, including in particular, substances in biological fluids, or cell and tissue extracts, for which an immunological counter-reactant can be produced.

The invention also includes a particle reagent comprising a polymer particle wherein the outermost layer of the particle has had its surface active functional groups initially reacted with a complementary functional group of a compound or analog of a molecule of biological interest. The remainder of the surface active functional groups have subsequently been reacted with a small molecular weight negatively charged compound as prepared by the method for increasing immunoassay activity and stability described above.

The invention also includes a method for measuring compounds of biological interest comprising the steps of incubating (1) a particle reagent having a negative charge on the outer shell of the particle surface and a functional group covalently bound directly or through a proteinaceous linker to a complementary functional group of a compound of biological interest, with (2) a liquid suspected of containing the compound of biological interest, and (3) an agglutinating agent; and, measuring the increase in particle size by photometric means. The compound of biological interest may be a drug; for example, those drugs selected from the group consisting of quinidine, phenobarbital and amino glycoside antibiotics, such as vancomycin, tobramycin and gentamycin. The polymer particle will have been treated after the coupling incubation step with a modifying agent selected from the group consisting of low molecular weight compounds having a functional group capable of both reacting with functional groups on the particle surface, such as epoxides, and also carrying a negative charge. These are anionic nucleophiles, preferably, β-mercaptoacetic acid and thiosulfate.

BRIEF DESCRIPTION OF THE DRAWINGS

The enhanced stability of particle reagents prepared by the method of the present invention is illustrated in the comparative graphs wherein.

DETAILED DESCRIPTION OF THE PREFERRED EMBODIMENTS

The present invention provides a process which not only achieves the objective of improving the stability of polymer particle reagents having functional groups on the outer shell of polymer particle, but also, most unexpectedly, enhances the immunoreactivity of these reagents. The process includes generally the step of treating the particle reagent, after the polymer particle is covalently bound to a compound of biological interest, with a modifying agent that will add a negative charge to the polymer surface under suitable pH and temperature conditions. Particle reagents thus treated demonstrate both greater stability and increased immunoreactivity as compared to untreated particle reagents. Incubation of the polymer particle reagent with a modifying agent, such as β-mercaptoacetic acid or thiosulfate, introduces anionic groups onto the polymer particle surface while simultaneously reducing the residual reactive groups, resulting surprisingly in both enhanced activity and improved stability. While other agents which modify the surface of the polymer particle to reduce reactive groups and introduce carboxyl groups may be used, it has been unexpectedly discovered that not all agents once thought useful for blocking residual reactive sites on a particle reagent will achieve both of the objectives of the invention. U.S. Pat. No. 4,480,042, for example, states that mercaptoethanol, mercaptopropionic acid, cysteine or a soluble polymer having amino functional groups may be used as blocking agents to bind and block unoccupied sites on the particle surface. It has been discovered, however, that mercaptoethanol treatment will improve stability in some particle reagents, but will not improve immunoreactivity, and in some cases may even cause a decrease in the activity of a particle reagent.

The polymer particle reagents which are the subject of the present invention are those useful in light scattering measurements of agglutination. There are a number of types of light scattering measurements of agglutination. They include turbidimetric detection, nephelometric detection, particle counting, quasielectric light scattering, autocorrelation spectroscopy and measurements of light scattering dissymmetry or polarization by particles. Each type of measurement system places different constraints on the particle reagents. The light scattering properties of particle suspensions depend on variables such as particle size, the refractive indices of the particle and the suspension medium, and the wavelength of light used for measurement. In all types of measurements, the higher the refractive index of particles at the chosen wavelength, the higher the light scattering signal. Wavelengths between about 400 to 650 nm are used during visual observation of agglutination reactions. During the agglutination reaction, the effective particle size increases. Small particles of high refractive index with short wavelength detection are preferred for high sensitivity in turbidimetric detection. For the measurement of samples in serum where proteins and other components absorb light, a convenient wavelength is one in excess of about 320 nm. For nephelometric detection, optimum sensitivity depends on the angle of measurement in addition to particle size and wavelength.

The polymer particle reagent to which the invention applies is a polymer particle having an inner core of a high refractive index and an outer shell covalently attached to a compound of biological interest, including antigen analogs or antibodies thereto. The antigen analog of the compound of biological interest is, for purposes of this invention, any substance or group of substances which share antigenic determinants and, therefore, behave substantially the same as the compound of biological interest with respect to binding specificity of the antibody to that compound of biological interest.

The inner core of the polymer particle can be selected from a large group of materials with high refractive index. Those materials that can be prepared by emulsion polymerization are preferred because of the ability to control particle uniformity and size. Because of the importance of the refractive index for light scattering agglutination assays such as turbidimetric detection, core materials must produce acceptable signal changes for the desired assay sensitivity. For analytes in high concentrations (the $\mu$g/mL range), the choice is not critical, but for analytes in the nanogram/mL range, particles having a high refractive index are necessary. The refractive index is a function of wavelength. The wavelength of the measurement, therefore, will affect the scattering properties. The refractive index is generally greater at shorter wavelengths. Preferably the inner core is a polymer having a refractive index of not less than 1.54 as measured at the wavelength of the sodium D line, 569 nm. Core polymers of high aromaticity and high atomic weight substituents are preferred over aliphatic polymers. The core monomers are selected from those which contain vinyl or allyl groups in addition to substituents such as halides, aromatic, heterocyclic, unsaturated or carbocyclic groups which impart high refractivity.

The outer shell is a polymer of an ethylenically unsaturated monomer which is formed by polymerization in the presence of the inner core and has functional groups capable of reacting with a complementary functional group of a compound of biological interest. The outer shell may optionally have other ethylenically unsaturated monomers in an amount sufficient to produce water insoluble polymer particles. Shell monomers containing, for example, an epoxy group include glycidyl methacrylate, glycidyl acrylate, vinyl glycidyl ether and methallyl glycidyl ether. Following the synthesis of the polymer particle, the compound of biological interest is covalently attached to the polymer particle to produce the desired particle reagent. The polymer particle reagents to which the invention applies may be made according to the procedures set forth in U.S. Pat. Nos. 4,401,765 and 4,480,042, the disclosures of which are incorporated herein by reference.

It is believed that the decrease in activity observed heretofore in particle reagents during storage may arise due to secondary binding between the compound of biological interest and unoccupied epoxide binding sites on the surface of the polymer. In the process of the present invention, the polymer particle reagent described above is incubated with a modifying agent for a period of time and under conditions conducive to reduction of the residual epoxides and addition of a negative charge, for example, by introduction of carboxyl groups on the polymer surface. The pH of the reaction will vary according to known limitations inherent in the compound of biological interest bound to the polymer particle. Guidance regarding selection of the optimum pH for reactions with compounds of biological interest is provided in J. F. King, R. Rathore, J. Y. L. Lamb, Z. R. Guo and D. F. Klassen,"pH Optimization of Nucleophilic Reactions in Water", Journal of the American Chemical Society, Vol.114, pp.3028–33 (1992).

The temperature of the reaction must be below the temperature that will cause the compound of biological interest to lose activity and above the temperature at which it will freeze. Preferred temperatures are between 4° to 100° C., more preferably above room temperature, and most preferably, between about 40° to 70° C. The reaction will proceed nicely, however, at room temperature, i.e., at about 20° C., and in some cases will work at 100° C. As stated, the limitations on temperature and pH depend on and will vary with, the particular compound of biological interest bound to the polymer particle. The temperatures and pH at which such compounds lose activity are known or can be determined with relative ease by well known techniques. The modifying agent has reactive functional groups thereon and is buffered during the incubation step with the particle reagent to maintain the pH above the pKa of the reactive functional group of the modifying agent.

The reaction is illustrated with an amine functional drug below. First, the polymer particle is covalently bound to the compound of biological interest, in this case a drug having an amine functionality.

Then, the reagent is reacted with the modifying agent, designated as X wherein R is a drug or drug analog, for example, vancomycin; and, X is a bifunctional compound of low molecular weight having a functional group bearing a negative charge and another functional group that is reactive with the particle.

The reactions above illustrate one complementary pair of general reactants (amines reacting with epoxides) that is suitable for linking the compound of biological interest to latex particles. Other complementary pairs suitable for coupling compounds of biological interest to epoxides include, among others, sulfhydryls, imides and phenols. Other complementary pairs of reactants that would be useful for coupling compounds of biological interest to particles are well known and include for example, without limitation, aldehydes and amines, aldehydes and thiols, chloromethylphenyl groups and amines, vinyl sulfones and thiols, amines and activated carboxyl groups.

Experiments were conducted with various drugs. The synthesis and testing of particle reagents using the amino glycoside antibiotic, vancomycin, and phenobarbital and quinidine follow.

EXAMPLES

Example 1

Amino Glycoside Antibiotic (Vancomycin) Reagent Modification

Materials and methods:

The materials used for the particle reagent synthesis were obtained from the Aldrich Co. with the exception of the vancomycin hydrochloride and fraction V bovine serum albumin (BSA), which were obtained from the Sigma Co., IBEX EP-110, a surfactant, which was obtained from the Rhone-Poulenc Co., and microbial inhibitors, which were obtained from the Supelco Co. Underivatized epoxide shell/core latex (epoxide latex) was prepared according to a previously published procedure set forth in U.S. Pat. No. 4,480,042. The antibody used for testing was obtained from a mouse hybridoma cell line obtained by fusion of spleen cells from mice that had been immunized with a vancomycin glutaraldehyde keyhole limpit hemocyanin immunogen. The antibody was an anti-vancomycin IgG1 type antibody. It was produced in mice, and isolated by protein A affinity purification. The antibody diluent was a 100 nM solution of sodium phosphate at pH 5.5, containing 150 mM sodium chloride and 1% fraction V BSA.

Diafiltration was done using a commercially available hollow fiber diafiltration cartridge. Centrifugation was done using a DuPont Sorval® RC28S centrifuge. The immunoassay testing was done using a Cobas Bio automated analyzer from the Roche Diagnostics Co. The analyzer was programmed to operate at 37° C. The detection wavelength was 340 nm. It first added a mixture of 51 $\mu$L of water followed by 150 $\mu$L of a mixture of particle reagent and assay buffer. The assay buffer was a mixture of 25 mM borax, 172 mM boric acid, 600 mM sodium chloride, and 1% of an anionic surfactant. A sample of 3 $\mu$L of calibrator followed by 20 $\mu$L of water was then added, and this mixture was incubated for 30 seconds. Calibrators were made from solutions of known quantities of vancomycin in pooled human serum. An optical density reading, identified as the "auxiliary read" and measured in absorbance units ((AU), where one AU equals the absorbance that will cause light to diminish by a factor of ten on a logarithmic scale), was taken, and then 10 $\mu$L of an antibody solution was added to start the reaction. After the reaction was started, readings were taken at 10 second intervals for four minutes. The assay response to the calibrators was calculated in one of two ways; either (i) by subtraction of the auxiliary read from the final reading, to give a four minute endpoint measurement, or (ii) by calculating the initial rates from the change in optical density during the first 10 seconds of reaction after the first reading, to give a rate measurement.

Reagent Synthesis a. Particle Reagent Synthesis

Two buffers were used in the synthesis. The first is coupling buffer (approx. pH 9.2), which was 50 mM sodium tetraborate decahydrate (19.05g/L) with 2.0% EP-110 (66.7 mL of the product, as received from the manufacturer, per liter of final mixture). The second buffer was reagent storage buffer, which was 15 mM, pH 7.8 phosphate buffer with 1.2% EP- 110. This was prepared by mixing 2.07g of NaH2PO4.H2O, 13.1mL of 1N NaOH, and 40.0 mL of EP-110 with water to make 1.0 L. 50 mL of 20% solids 65 nm epoxide latex was mixed with 46 mL of coupling buffer. To this suspension, a solution of 400 mg of vancomycin hydrochloride in 4 mL of water was added with stirring. This mixture was heated in a circulating water bath for 22 hours at 40° C. The product was purified by diafiltration using an H1MPO 1-43 hollow fiber cartridge, using an operating pressure of 10 psi, a working volume of 150–190 mL of latex. Wash buffer, composed of a 1:1 mixture of coupling buffer and storage buffer described above was added at the same rate that effluent was collected. After 2 L of effluent was collected, the makeup buffer was switched from wash buffer to pure storage buffer. 600 mL of storage buffer was eluted before the process was stopped. The purified latex was concentrated, the diafiltration cartridge was rinsed with storage buffer, and the final volume of the concentrate and rinses was brought to 200 mL. This reagent is identified in the subsequent sections of Example 1 as reagent 1A.

b Post Synthesis Chemical Modification

Two 10 mL aliquots of reagent 1A were centrifuged at 28,000 RPM for one hour to give a clear supernatant, which was decanted and discarded. The latex particle pellet from one sample was resuspended, with stirring in coupling buffer, and the other was resuspended in coupling buffer (borate) containing 100 mM sodium β-mercaptoacetate (BMA) (11.4 g/L). Both latexes were incubated for 18 hours at 40 C, and then centrifuged as above, resuspended to the same volume with storage buffer, centrifuged a second time, and resuspended a second time to the same volume with storage buffer. These products are identified as reagents 2A and 2B, respectively, in subsequent sections of Example 1.

Reagent Testing c. Comparative Activity Reagent Testing

The particle reagents were each diluted ⅟45 into assay buffer. This concentration of reagent gave an optical density of approximately 1 AU with a 1 cm pathlength, when tested on the Cobas Bio automated analyzer. The concentration of antibody used in the antibody reagent was 111 μg/mL. Reagents 1A, 2A, and 2B were tested using the assay conditions described above for the rate mode of detection. The standard curves obtained are shown below in Table 1:

TABLE 1

| Vancomycin, concentration in calibrator μg/mL | Reagent 1A, no treatment (mAU/min) | Reagent 2A, Borate Only (mAU/min) | Reagent 2B, BMA and Borate Treatment (mAU/min) |
|---|---|---|---|
| 0 | 723 | 529.2 | 1147.8 |
| 2.5 | 511.2 | 347.4 | 772.2 |
| 6.3 | 302.4 | 214.2 | 467.4 |
| 10 | 177.6 | 126 | 272.4 |
| 25 | 37.2 | 22.2 | 60.6 |
| 40 | 11.4 | 9.6 | 25.2 |

Figure 2:
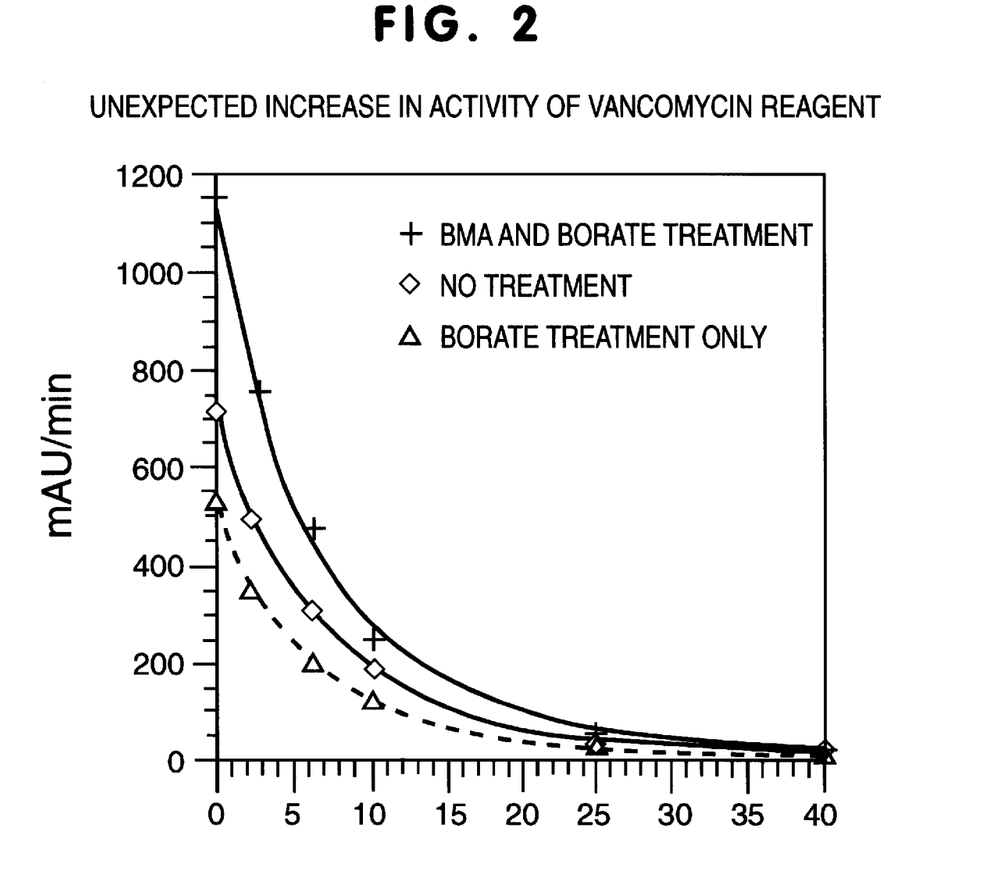
FIG. 2 illustrates the unexpected increase in activity of the vancomycin reagent treated with β- mercaptoacetic acid and borate.

FIG. 2 illustrates the improved activity of the reagent treated with BMA. The top curve is the particle reagent after treatment with BMA in borate buffer. The second curve is the untreated reagent and the bottom curve is the reagent treated with borate buffer alone. The expected result is the activity obtained with borate buffer treatment. The unexpected result is represented by the top curve; the increase in activity for reagents treated with BMA. Loss of activity is expected because vancomycin is known to rearrange under the conditions of the reaction. The vancomycin reagent treated with BMA in borate buffer demonstrated increased activity.

d. Comparative Stability Reagent Testing

Figure 1A:
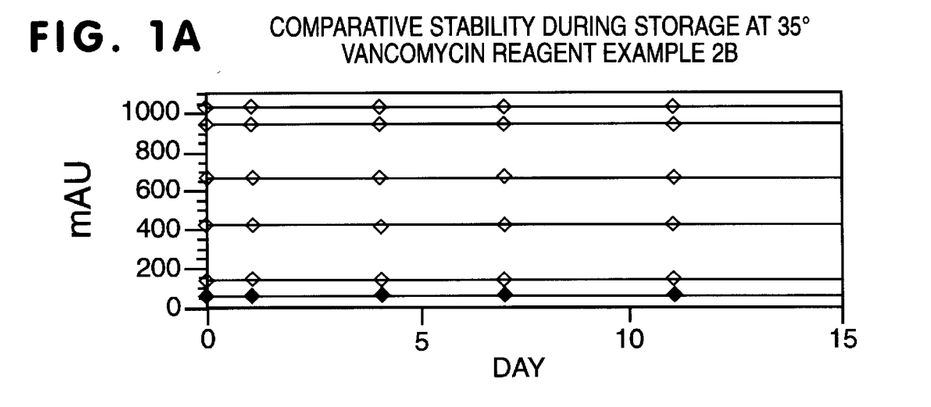
FIG. 1A illustrates the stability of a vancomycin reagent treated with β-mercaptoacetic acid in borate and stored at 35° C.
Figure 1B:
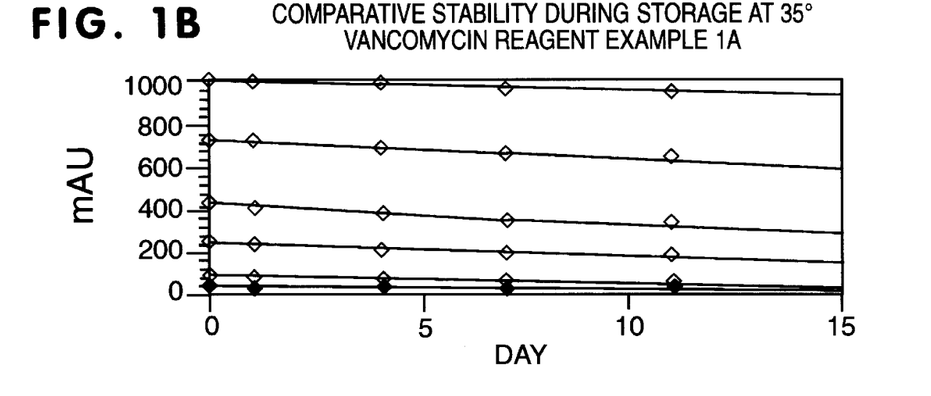
FIG. 1B illustrates the stability of an untreated vancomycin reagent stored at 35° C.
Figure 1C:
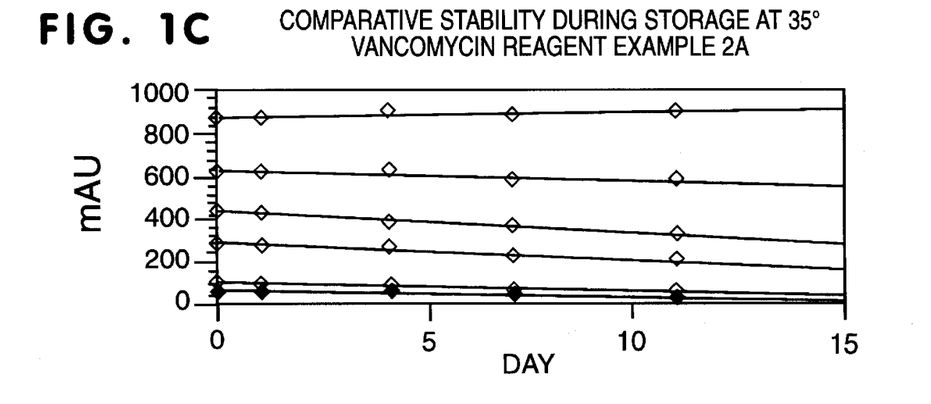
FIG. 1C illustrates the stability of a vancomycin reagent treated in borate buffer alone and stored at 35° C.

Samples of each of reagents 1A, 2A and 2B described above were stored at 35° C., while all other reagents were stored at 4° C. Samples were taken and used in assays for vancomycin, as described above. In this case, the data in the comparison was taken using the four minute endpoint assay response model described above. The assays were done on days 0, 1, 4, 7, and 11 after the particle reagents were placed in 35° C. storage. The object of the assay is to determine if the agglutination reaction proceeds at the same rate on subsequent days as it did on day 0. The response of each of the reagents is shown in FIGS. 1A, 1B and 1C. In this series of graphs, the assay response, in mAU, is shown for each day of testing. The figures demonstrate the enhanced stability of the vancomycin reagent treated with BMA as compared to the untreated vancomycin reagents. The activity of the vancomycin reagent treated with BMA was the same on days 1, 4, 7 and 11 as it was on day 0, demonstrating the stability of the reagent over time when stored at a cool temperature. FIG. 1B demonstrates the loss of activity over time when the vancomycin reagent is untreated. The samples of untreated reagents (♦) stored at 4° C. appeared to be stable after 11 days, but the sample stored at 35° C. (♦) lost about 20% of its activity over that same period. The vancomycin reagent treated only with borate buffer also decreased in activity over time for mAU up to 640 on day 0 and increased over time for mAU over 850 on day 0. Increases or decreases in activity are undesirable. The activity of the particle reagent should remain constant notwithstanding storage over periods of time. Post synthesis modification of the particle reagent by treatment with a modifier, such as BMA, provides both the desired stability and increased immunoreactivity.

Example 2

Quinidine Assay a. Particle Reagent Synthesis

Quinidine particle reagent was synthesized from the coupling of a quinidine derivative onto a core/shell latex particle. The core/shell latex particle is composed of a high refractive index polystyrene core and a glycidyl methacrylate shell crosslinked with ethylene glycol dimethacrylate. Epoxide functional groups on the particle surface are amenable to reaction with nucleophilic moieties. The quinidine derivative used was an amino-containing adduct between 11-(2-carboxyethylthio)dihydroquinidine (QAD) and a spacer group (2,2'-(ethylenedioxy)diethylamine).

QUINIDINE
($C_{20}H_{24}N_2O_2$)

-continued

QAD
($C_{23}H_{30}N_2O_4S$)

QAD is made by the free radical addition of 3- mercaptopropionic acid to the quinidine double bond, using 2,2'-azobis(isobutyronitrile) as the initial free radical source.

b. Post Synthesis Chemical Modification

A sample of the quinidine particle reagent synthesized by the process described in section a of Example 2 was put aside as control. Particle reagents with the surface epoxide inactivated were prepared by the following quench procedure. Quinidine particle reagent (5.0 mL) samples were centrifuged and the supernatant discarded. The solids were resuspended into quench buffer (5 mL, 50 mM sodium carbonate solution, pH 9.0). The modifying agent (sodium mercaptoacetic acid, 43 mg, or sodium thiosulfate pentahydrate, 48 mg') was subsequently added. The pH of each reaction was adjusted to 9.5. The mixtures were mixed, then incubated for 16 hours at 70° C. The various quinidine particle reagents were then purified by centrifugation and resuspension (3×) into particle wash buffer (15 mM phosphate buffer, 1.0% of an anionic surfactant, pH 7.4). The final pellets were resuspended into particle storage buffer (15 mM phosphate buffer, 0.5% anionic surfactant) and sonicated until absorbance ratio, A340/A600, is above 10.0.

c. Assay Analysis

The resulting particle was diluted (1:50 giving absorbance at 340 nm of 1 AU) into phosphate assay buffer (105 mM, pH 7.0, 0.4% of an anionic surfactant, 0.002% thimerosal). Antibody reagent was an ascites sample of monoclonal antibody (5 mg/mL, diluted 1:45 into 50 mM sodium phosphate buffer, 75 mM sodium chloride, 0.1% sodium azide, 0.05% thimerosal at pH 6.7). Quinidine calibrators for the DuPont aca® Discrete Clinical Analyzer were utilized to generate the standard curves. Turbidimetric immunoassays were performed on a Cobas Bio clinical analyzer from Roche Diagnostics Co. at 37° C. utilizing the end point type of measurement described in Example 1, modified as follows: Particle reagent (240µL), sample (4µL), and water (14µL) were incubated (30 secs). The reaction was initiated with anti-quinidine (20µL with 20µL water flush). The reaction rate was calculated by subtracting the initial auxiliary reading from the end point over a 220 second interval. Aggregation responses to various calibration levels of the quinidine particle reagent control versus a reagent modified via BMA are shown in Table 2.

TABLE 2

Quinidine Assay Results for Control and BMA or Thiosulfate Treated Particle Reagents Particles

| Quinidine Calibrator (µg/mL) | Control | BMA |
|---|---|---|
| 0.0 | 347 | 439 |
| 0.5 | 326 | 430 |

TABLE 2-continued

Quinidine Assay Results for Control and BMA or Thiosulfate Treated Particle Reagents Particles

| Quinidine Calibrator (µg/mL) | Control | BMA |
|---|---|---|
| 1.0 | 315 | 420 |
| 2.0 | 286 | 399 |
| 4.0 | 244 | 350 |
| 8.0 | 199 | 292 |

The results demonstrate that reagents treated with the β-mercaptoacetic acid after reagent synthesis have markedly improved activity as compared to the control. The increased agglutination signal is confirmed to be immunospecific, as a decreased antibody concentration will reestablish a calibration standard curve equal to that of the control particle sample.

Example 3

Phenobarbital Assay a Particle Reagent Synthesis

Coupling buffer (164 mL, 20 mM borate buffer, 0.3% IBEX EP-110, 0.005% thimerosal, pH 8.0), phenobarbital/PEPA conjugate (12mL of a 10% DMSO solution, adduct between phenobarbital 3-(5-valeric) acid and polyethylene polyamine linker), and particle raw material (24 mL at 20% solids, 70 mn polystyrene/ polyglycidylmethacrylate core/shell latex particle) were added sequentially to a reaction vessel. The pH was adjusted to 8.0. The solution was heated for six hours at 70° C. The pH was then adjusted to 6.5. This particle solution was then purified via solvent diafiltration (2L of 20 mM borate buffer, 0.30% IBEX EP-110, 0.005% thimerosal, pH 8.0) across a hollow-fiber column (Amicon 0.10µcartridge). This was followed by a second diafiltration into the particle storage buffer (1.2L of 5 mM citrate buffer, 0.30% IBEX EP-110, pH 5.5). The resultant particle residue was brought up to 200 mL in the particle storagebuffer.

Phenobarbital 3-(5-valeric acid) may be prepared from a substitution reaction between phenobarbital and ethyl 5-bromovalerate followed by hydrolysis of the ester. These types of reactions are described in J. March,"Advanced Organic Chemistry," pp.357, 349 (McGraw-Hill pub. 1977). The polyethylene polyamine linker has been previously described in U.S. Pat. No. 4,581,337 to W. A. Frey and D. M. Simons.

b. Post Synthesis Chemical Modification

To each reaction vessel were added sequentially water (0.5 mL), phenobarbital particle reagent (2.0 mL), and quench buffer (2.5 mL, 100 mM phosphate buffer, 2% IBEX EP-110, pH 6.5). One control was put aside at this stage per experiment. The samples to be quenched were further treated with (i) BMA (57 mg) or (ii) sodium thiosulfate pentahydrate (124 mg) or (iii) a mixture of 5,5-dithiobis(2-nitrobenzoic acid) (DTNB) (50 mg) and dithiothreitol (DTT) (19 mg), or (iv) a mixture of DTNB (50 mg) and DTT (19 mg) and β-mercaptoethanol (2ME) (9µL). The pH of each reaction was adjusted to 6.5. The mixtures were stirred, then incubated for 1.5 hours at 70° C. The various phenobarbital particle reagents were then purified by centrifugation and resuspension (3×) into particle storage buffer.

c. Assay Analysis

Turbidimetric immunoassays were performed on a DuPont Dimension® Clinical Analyzer. A general protocol involves suspension of phenobarbital particle reagent (40µL, diluted 1:5 into particle diluent) and water (40µL) into assay buffer (150 µL, 200 mm phosphate buffer, 0.64% anionic surfactant, about 0.01% antimicrobial preservative, pH 7.0). The reaction is initiated by the addition of anti-phenobarbital monoclonal antibody (approximately 10 µg/assay in 40 µL of 10 mM phosphate buffer, 1 M sodium chloride, about 0.01% antimicrobial preservative, 1% BSA) and water (40, µL). The reaction rate was calculated using the end point method of measurement in mAU per 240 seconds.

The turbidimetric immunoassay results for a control and phenobarbital particle reagent with epoxide treated via either BMA or thiosulfate are reported in Table 3. The results set forth in Table 3 show that post synthesis chemical modification with both BMA and thiosulfate increased the activity of the phenobarbital reagent. Treatment with thiosulfate gave better results for the phenobarbital particle reagent than treatment with BMA.

TABLE 3

Phenobarbital Assay Result:
Control vs. BMA or Thiosulfate Treatment

| Calibrator | Phenobarbital Particles | | |
|---|---|---|---|
| (µg/mL) | Control | BMA | Thiosulfate |
| 0 | 295 | 345 | 395 |
| 10 | 197 | 241 | 411 |
| 20 | 136 | 167 | 416 |
| 40 | 78 | 94 | 368 |
| 80 | 39 | 45 | 218 |

Note: Phenobarbital Particles were prepared according to standard loading procedures followed by a quenching step to eliminate surface active epoxide groups using BMA or thiosulfate.

The turbidimetric immunoassay results for a control and phenobarbital particle reagent with epoxide treated via either mixtures of DTNB and DTT or DTNB, DTT, and 2ME are reported in Table 4. These results demonstrate that other negatively charged modifying agents will improve activity. It was found in separate testing, however, that treatment with 2ME alone will not improve activity.

TABLE 4

Phenobarbital Assay Results:
Control vs. DTNB/DTT or DTNB/DTT/2MB
Quenched Particles at Identical Antibody Concentration

| Calibrator | Phenobarbital Particles | | |
|---|---|---|---|
| (µg/mL) | Control | DTNB/DTT | DTNB/DTT/2MB |
| 0 | 225 | 419 | 417 |
| 10 | 143 | 418 | 410 |
| 20 | 98 | 420 | 406 |
| 40 | 56 | 433 | 411 |
| 80 | 29 | 394 | 423 |

Note: Phenobarbital Particles were prepared according to standard loading procedures followed by a treatment step to eliminate surface active epoxide groups using mixtures of DTNB, DTT, and 2ME.

The thiosulfate activity values in Table 3 are high for calibration values 0, 10 and 20. To demonstrate that the values are attributable to thiosulfate treatment and not to nonspecific aggregation, the assay stoichiometry was re-optimized. Standard curves with enhanced signals were obtained by further dilution of the antibody reagent in the assay. The standard curve optimization results for the thiosulfate treated particle are shown in Table 5. Similarly, the standard curve optimization results for the DTNB/DTT and the DTNB/DTT/2ME treated particles are shown in Table 6.

TABLE 5

Assay Standard Curve Optimization
Results for Thiosulfate Particle

| Calibrator | Thiosulfate Treatment Ab Dilutions | | | |
|---|---|---|---|---|
| (µg/mL) | 1:30 | 1:50 | 1:70 | 1:100 |
| 1 | 394.5 | 387.5 | 295.6 | 172.8 |
| 10 | 410.9 | 337.1 | 237.3 | 135.5 |
| 20 | 416.3 | 278.2 | 194.1 | 111.2 |
| 40 | 367.6 | 188.8 | 133.3 | 77.4 |
| 80 | 217.7 | 101.7 | 70.4 | 43.8 |

Note: Thiosulfate treated particles with enhanced standard curve signal were re-optimized to provide a normal standard curve shape by further dilution of the antibody reagent.

TABLE 6

Assay Standard Curve Optimization Results
for DTNB/DTT or DTNB/DTT/2MB Treated Particles

| | Ab Dilutions | | | | | |
|---|---|---|---|---|---|---|
| Calibrator | 1:30 | 1:60 | 1:90 | 1:30 | 1:60 | 1:90 |
| (µg/mL) | DTNB/DTT | | | DTNB/DTT/2ME | | |
| 0 | 419 | 427 | 421 | 417 | 421 | 327 |
| 10 | 418 | 406 | 367 | 410 | 417 | 291 |
| 20 | 420 | 364 | 313 | 406 | 391 | 245 |
| 40 | 433 | 264 | 232 | 411 | 206 | 170 |
| 80 | 394 | 143 | 137 | 423 | 171 | 91 |

Note: Both DTNB/DTT and DTNB/DTT/2ME treated particles with enhanced standard curve signals were re-optimized to provide a normal standard curve shape by further dilution of the antibody reagent.

The various samples were stored at 35° C. and tested as described in Example 1 for stability. The results are tabulated in Table 7.

TABLE 7

Accelerated Calibration Stability
for Phenobarbital Particle Reagents

| PHNO PR Quenchers: | Stability Slope Results Sorted by First Calibrator Calibrators | | | | |
|---|---|---|---|---|---|
| Quench Reagent | 0 | 10 | 30 | 40 | 80 |
| β-Mercaptoethanol (2ME) | −0.62% | −0.20% | 0.09% | 0.11% | −0.29 |
| Thiosulfate, Sodium 5.H$_2$o | −0.22% | −0.24% | −0.12% | −0.02% | 0.29% |
| a-Monothioglycerol | −1.10% | −0.71% | −0.22% | 0.23% | 1.00% |
| β-Mercaptoacetic Acid, Sodium (BMA) | −2.07% | −2.19% | −2.04% | −1.68% | −1.38% |
| Control, Unprocessed | −2.49% | −2.34% | −2.19% | −1.78% | −1.47% |
| DTNB/DTT/2ME | −1.95% | −3.29% | −4.07% | −4.81% | −5.20% |
| DTNB/DTT | −3.82% | −4.94% | −5.58% | −6.20% | −6.50% |

The stability values in Table 7 represent a percent shift from 0. As stated above with respect to FIGS. 1A, B and C, a stable reagent should have no change in activity which would provide a 0% change. Increases in activity are represented by positive numbers. Decreases in activity are represented by negative numbers. The unprocessed control sample in Table 7 represents the base line. Reagents treated with the modifying agents identified above the control in Table 7 are considered to behave better than the control. The reagents treated with modifying agents below the control were less stable than the control. Treatment of particle reagents in Table 7 with 2ME and monothioglycerol alone increased the stability of the reagents. However, the results of assays to compare the activity of the 2ME and monothioglycerol treated reagents with the untreated control reagent showed no significant change in activity. Thus, only post synthesis modification with BMA or thiosulfate both enhanced the stability over time and increased the activity of the phenobarbital particle reagents. BMA or thiosulfate treatment adds a negative charge to the polymer surface. 2ME and monothioglycerol treatment under the conditions of the reaction defined herein do not.

Post synthesis modification of particle reagents with BMA enhanced stability and, surprisingly, improved the immunoactivity in all the particle reagents tested. Thiosulfate treatment did not improve the activity of the quinidine particle reagent but did improve the activity and stability of the phenobarbital particle reagent.

What is claimed is:

1. A method for increasing the activity and the stability of a particle reagent wherein the reagent comprises a polymer particle having surface active functional groups on an outer layer thereof capable of reacting with a complementary functional group of a compound of biological interest, and which is covalently bound to the compound of biological interest, the method comprising:
   the step of incubating said particle reagent at a predetermined pH and temperature with a modifying agent comprising an anionic nucleophile selected from the group consisting of β-mercaptoacetic acid and thiosulfate capable of placing a negative charge and reducing unreacted functional groups on the outer layer of the polymer particle.

2. The method recited in claim 1 wherein said compound of biological interest is a quinidine and said modifying agent is β-mercaptoacetic acid.

3. The method recited in claim 1 wherein said compound of biological interest has a molecular weight of less than 2000.

4. The method recited in claim 1 wherein said modifying agent has functional groups and is buffered during the incubation step to maintain a pH above the pKa of the reactive functional group of the modifying agent.

5. The method recited in claim 1 wherein the temperature is within the range of 4° to 100° C.

6. A method for measuring compounds of biological interest comprising the steps of incubating:
   (1) the polymer particle reagent comprising on an outer layer thereof (a) an active functional group covalently bound directly or through a proteinaceous linker to a complementary functional group of a compound of biological interest, and (b) a second functional group comprising an anionic nucleophile selected from the group consisting of β-mercaptoacetic acid and thiosulfate capable of placing a negative charge and reducing unreacted functional groups on the outer layer of the polymer particle with
   (2) a liquid suspected of containing the compound of biological interest, and
   (3) an agglutinating agent; and, measuring increase particle size by photometric means.

7. The method of claim 6 wherein the compound of biological interest is a drug selected from the group consisting of amino glycoside antibiotics, quinidine and phenobarbital.

8. The method recited in claim 7 wherein the amino glycoside antibiotics comprise vancomycin, tobramycin and gentamycin.

9. The method recited in claim 6 wherein the second functional group on the outer layer of the polymer particle is prepared with a modifying agent for reducing the second functional group on the outer layer after the covalent attachment of the compound of biological interest to the active functional group.

10. A particle reagent comprising a polymer particle having an outer layer having a functional group covalently bound directly or through a proteinaceous linker to a complementary functional group of a compound of biological interest, said particle reagent being prepared by a method comprising:
    incubating at a predetermined pH and temperature (1) a polymer particle having a functional group capable of reacting with a complementary functional group of a compound of biological interest wherein the complementary functional group is covalently bound to the compound of biological interest, with (2) a modifying agent comprising an anionic nucleophile selected from the group consisting of β-mercaptoacetic acid and thiosulfate capable of placing a negative charge and reducing unreacted functional groups on the outer layer of the polymer particle.

11. The particle reagent recited in claim 10 wherein said compound of biological interest is a drug.

12. The particle reagent recited in claim 11 wherein said drug is selected from the group consisting of amino glycoside antibiotics, quinidine, and phenobarbital.

13. A method for producing a particle reagent, the reagent comprising (1) a polymer particle having an outer shell wherein the outer shell has a functional group capable of reacting with a complementary functional group of a compound of biological interest, and (2) the compound of biological interest, the method comprising the steps of:
    synthesizing particle reagents by covalently binding reactive functional groups of polymer particles to complementary functional groups of compounds of biological interest, then incubating the polymer particle reagents under predetermined pH and temperature conditions with a modifying agent comprising an anionic nucleophile selected from the group consisting of β-mercaptoacetic acid and thiosulfate for a period of time sufficient to permit said modifying agent to reduce unreacted functional groups on the surface of said outer shell of said polymer particles and place a negative charge thereon.

14. The method recited in claim 13 wherein said compound of biological interest is a drug selected from the group consisting of amino glycoside antibiotics, quinidine, and phenobarbital.

15. The method recited in claim 13 wherein said modifying agent has a reactive functional group and is buffered during the incubating step to maintain a pH above the pKa of the reactive functional group of the modifying agent.

16. The method recited in claim 13 wherein the temperature is within the range of 4° to 100° C.

* * * * *

UNITED STATES PATENT AND TRADEMARK OFFICE
CERTIFICATE OF CORRECTION

PATENT NO : 5,854,083

DATED : December 29, 1998

INVENTOR(S) : Victor Pichai Chu, et, al.

It is certified that errors appear in the above-identified patent and that said Letters Patent is hereby corrected as shown below:

Column 11, Line 44: Delete "2MB" and insert --2ME--.

Column 11, Line 49: Delete "2MB" and insert --2ME--.

Column 12, Line 21: Delete "2MB" and insert --2ME--.

Signed and Sealed this

Thirty-first Day of August, 1999

Attest:

Q. TODD DICKINSON

*Attesting Officer*     *Acting Commissioner of Patents and Trademarks*